United States Patent [19]

Daniels

[11] 4,144,880

[45] Mar. 20, 1979

[54] ORTHOPEDIC TABLE

[76] Inventor: E. Robert Daniels, 638 W. Duarte Rd., Arcadia, Calif. 91006

[21] Appl. No.: 776,862

[22] Filed: Mar. 11, 1977

[51] Int. Cl.[2] .......... A61F 5/00

[52] U.S. Cl. .......... 128/71; 128/74

[58] Field of Search .......... 128/70, 71, 72, 73, 128/74, 78, 69, 25 R; 269/322, 323, 324, 325, 326; 5/62

[56] References Cited

U.S. PATENT DOCUMENTS

| | | | |
|---|---|---|---|
| 30,588 | 11/1860 | Pitts | 128/71 |
| 176,540 | 4/1876 | McArthur | 5/62 |
| 1,938,006 | 12/1933 | Blanchard | 128/74 |
| 1,950,948 | 11/1929 | Murray | 128/72 |
| 2,262,271 | 11/1941 | De Camp | 128/74 |
| 2,273,088 | 2/1942 | Byers | 128/25 R |
| 2,577,177 | 12/1951 | Anderson | 269/322 |
| 2,768,622 | 10/1956 | Sanders | 128/25 R |
| 3,420,229 | 1/1969 | Miller | 128/71 |
| 3,741,200 | 6/1973 | Morin | 128/71 |
| 3,766,912 | 10/1973 | Daniels | 128/71 |

FOREIGN PATENT DOCUMENTS

| | | | |
|---|---|---|---|
| 1121687 | 1956 | France | 128/71 |

*Primary Examiner*—Robert W. Michell
*Assistant Examiner*—Arthur S. Rose
*Attorney, Agent, or Firm*—Christie, Parker & Hale

[57] ABSTRACT

An orthopedic table for applying controlled flexion and traction to a patient's body includes a table divided at its mid-region into upper and lower platforms. A patient lying on the table is harnessed at the opposite ends of the table, and pelvic straps on the lower platform secure the patient's pelvic region to the lower platform. The platforms pivot simultaneously to periodically lower the central region of the table and separate the inner edges of the platforms. The support provided by the pelvic straps enables the lowered platforms to periodically force the patient's lower back into flexion in the separation space between the platforms. The remote end of the lower platform is adjustable in elevation to control the pull on the patient's hamstrings which, in turn, controls the amount of flexion exerted on the patient's lower back. The patient's head or arms can be selectively harnessed at the head of the upper platform to place the patient's upper body in traction during lowering of the platforms. A harness for the patient's head is secured to a vertically adjustable support for controlling the amount of flexion applied to a patient's neck during lowering of the table. A harness for the patient's arms also has a vertically adjustable support to control the amount of flexion applied to the patient's shoulders. The amount of traction applied by either harness is adjustable, and the head harness is rotatable to either side during lowering of the platforms to increase rotational freedom of the patient's neck.

28 Claims, 9 Drawing Figures

Fig. 7
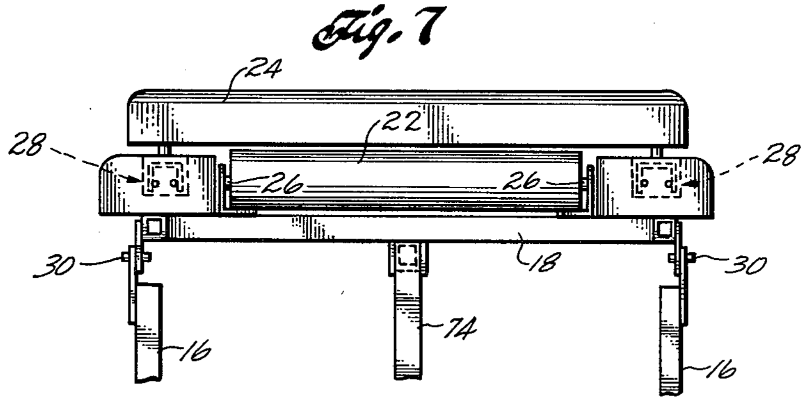
Fig. 8
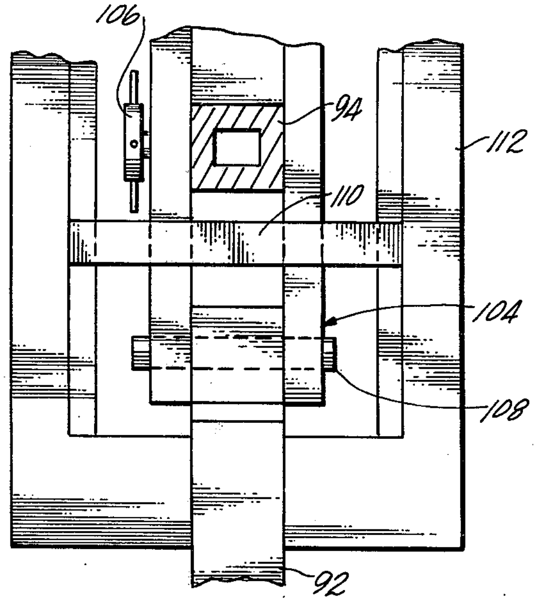
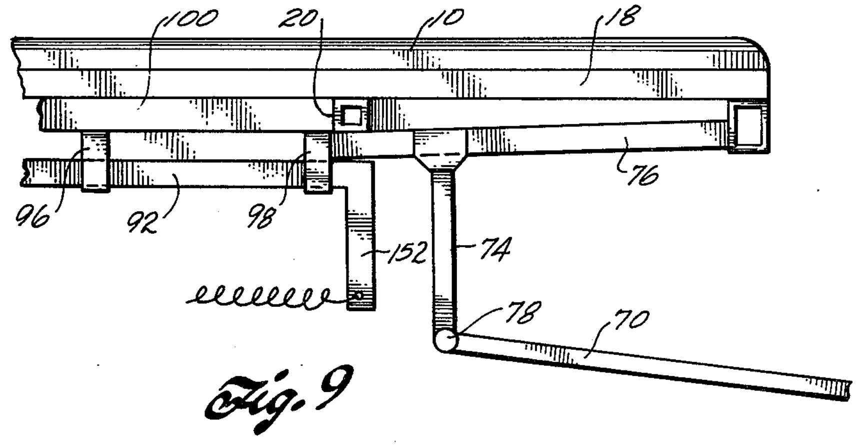
Fig. 9

ORTHOPEDIC TABLE

BACKGROUND

This invention relates to orthopedic tables, and more particularly to an improved orthopedic table for applying controlled traction to a patient's body and for applying controlled flexion to the lower back, shoulders and neck of a patient.

This invention represents an improvement over the orthopedic traction table disclosed in my U.S. Pat. No. 3,766,912.

Pathology of the lower back, neck and shoulders usually results in contractures or tightness of the soft tissues involved in these areas. The orthopedic table disclosed in my U.S. Pat. No. 3,766,912 partially relieves such contractures by stretching the contracted tissues and hamstrings by applying traction to the patient's upper and lower body. However, the amount of traction is not readily controllable, and more importantly, the table does not apply a predetermined, localized amount of flexion to the patient's lower back, shoulders or neck. It also does not relieve limited rotation of the neck or provide selected stretching of the hamstrings.

The present invention is based on a recognition of the importance of applying complete flexion to the lower back, shoulders and neck to relieve contractures in these areas. In lower back pathology there is typically a loss of flexion of the lumbar spine and tightness of the hamstrings. Pathology of the cervical spine produces limitation of flexion and rotation of the neck, and shoulder pathology commonly involves loss of flexion of the shoulders. The present invention provides an effective means of relieving contractures of the lower back, shoulders and neck by accomplishing complete flexion to these areas as well as rotation to the neck. This enables the patient to recover complete motion of these areas, which not only relieves contractures, but prevents progression of pathology in these areas.

The orthopedic table disclosed in my patent provides progressively less support for the patient's weight as the table is lowered. Thus, the patient's body weight affects the amount of traction applied to the patient. As a result, it is difficult to precisely control the amount of traction applied to each patient. The present invention applies traction to a patient's body substantially independently of the patient's body weight. This enables the physician to accurately control the amount of traction applied to each patient.

SUMMARY OF THE INVENTION

Briefly, according to a presently preferred embodiment of this invention, an orthopedic table is divided at its mid-region to form an upper platform and a lower platform. Each platform is tilted to increase the mid-region separation between the platforms. A lower portion of the patient's body is held in a fixed position on the lower platform, and an upper portion of the patient's body is held in traction on the upper platform. Pelvic straps secured to the lower platform extend under a rear pelvic region of the patient's body and over a front pelvic region of the patient. The pelvic straps hold the pelvis of the patient in a fixed position on the lower platform during mid-region separation of the platforms. The pelvic straps also increase the pressure on the front pelvic region of the patient during lowering of the platforms. This forces the patient's lower back region into flexion in the separation space between the platforms.

Preferably, the lower platform can be releasably secured in a desired angular orientation during separation of the platforms. This selectively controls the amount of pull on the patient's hamstrings which, in turn, adjusts the amount of flexion applied to the patient's lower back.

In a preferred form of the invention, controlled flexion can be selectively applied to the neck or shoulders. To apply flexion to the neck, the patient is held in traction on the upper platform by a head harness. The harness is attached to a support which is adjustable in elevation to, in turn, apply a selected amount of flexion to the patient's neck region during lowering of the platforms. To apply flexion to the shoulders, the patient's arms are held in traction on the upper platform by a harness attached to a support which is adjustable in elevation. This, in turn applies a selected amount of flexion to the patient's shoulders during lowering of the platforms.

In one embodiment of the invention, the inner marginal edge of the lower platform moves in a generally linear direction during lowering of the platforms. This motion, combined with the pelvic strap means of support, applies traction to the patient's body essentially independently of the patient's body weight and in a relatively constant manner.

Preferably, the patient's upper body is supported either by a head harness, or by a harness secured to the patient's arms. Either harness is capable of applying an adjustable amount of traction force to the patient's upper body during lowering of the platforms.

The invention enables the physician to apply controlled amounts of flexion to the patient's lower back, shoulders and neck regions, as well as separately controlling the amount of traction applied to the patient. This enables the physician to easily, as well as accurately, control the type of treatment which best suits each patient's symptoms.

These and other aspects of the invention will be more fully understood by referring to the following detailed description and the accompanying drawings.

DRAWINGS

FIG. 7 is a fragmentary elevation view taken on line 7—7 of FIG. 2;

FIG. 8 is a fragmentary top plan elevation view, partly in cross-section, taken on line 8—8 of FIG. 2; and FIG. 9 is a fragmentary elevation view, partly in cross-section, taken on line 9—9 of FIG. 4.

DETAILED DESCRIPTION

An orthopedic table according to this invention includes an elongated table divided at its mid-region to form an upper platform 10 and a lower platform 12. The platforms are supported by a skeleton framework enclosed in a rectangular skirt formed by upright side panels 14. The skeleton framework includes a mechanism for tilting the upper and lower platforms about corresponding longitudinally spaced apart transverse axes. The mechanism for tilting the platform is described below.

Figure 2:
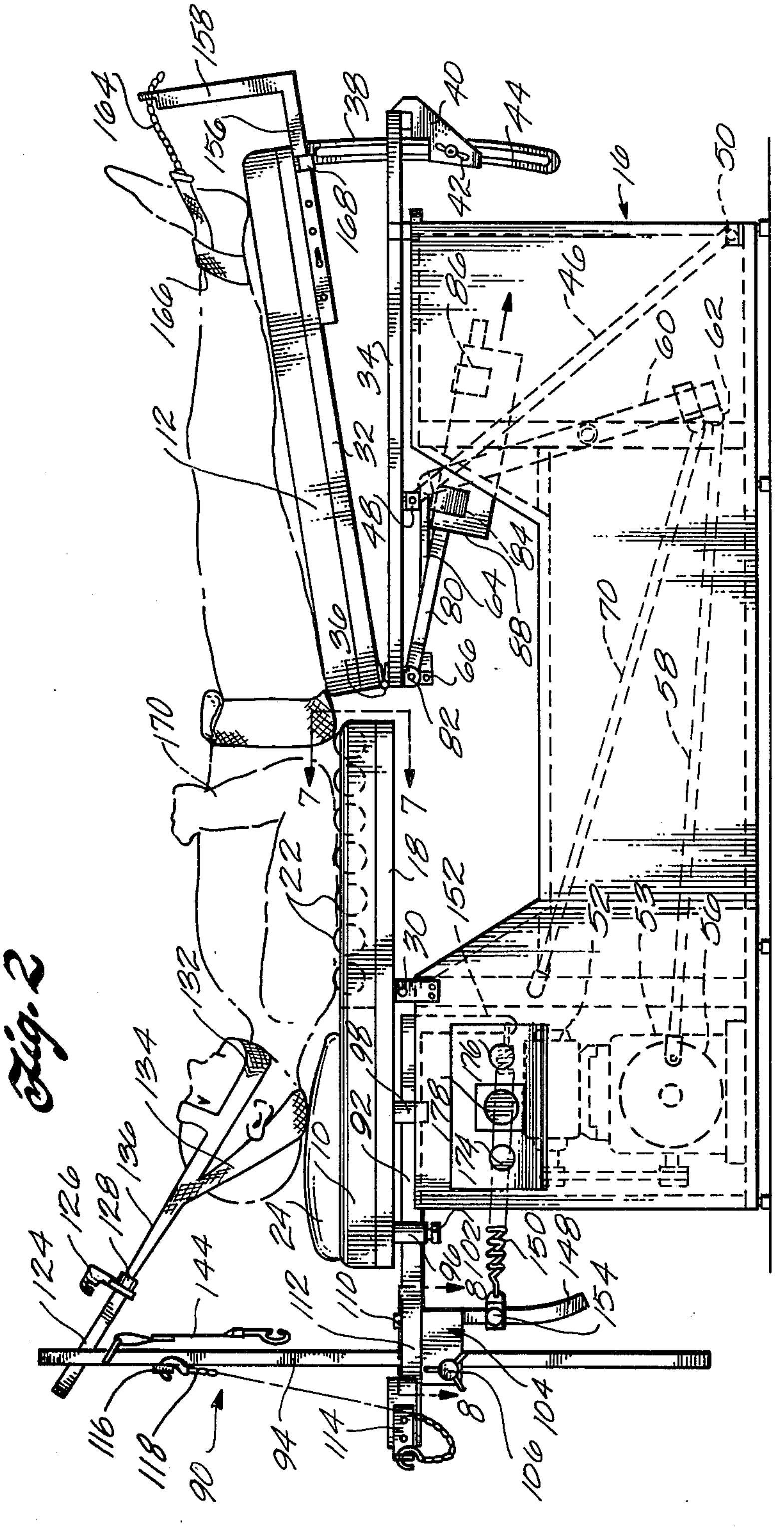
FIG. 2 is an elevation view taken on line 2—2 of FIG. 1 and showing a patient in a rest position on the table.

The upper and lower platforms 10 and 12 are adapted to lie in a relatively horizontal plane, also referred to as the rest position of the table (shown in FIG. 2). In the rest position the lower platform 12 may be elevated at its outer end, as shown in FIG. 2. In the rest position there is a small space between the inner marginal edges of the platforms. The platforms pivot between an essentially horizontal position and a tilted position in which the head of the upper platform 10 and the foot of the lower platform 12 are elevated relative to the inner marginal edges of the platforms. During tilting the separation space between the inner marginal edges is increased and the inner edges of the platforms move downwardly relative to the outer edges of the platforms. In the lower position the inner edge of the lower platform is higher than that of the upper platform. A patient to be treated (represented in phantom lines at 15) lies on the table with the upper portion of his body on the upper platform 10 and the lower portion of his body on the lower platform 12. The platforms are tilted in unison between theii elevated and rest positions so as to periodically form a lowered separation space between the tilted platforms. The purpose of this platform movement will be described below.

Figure 3:
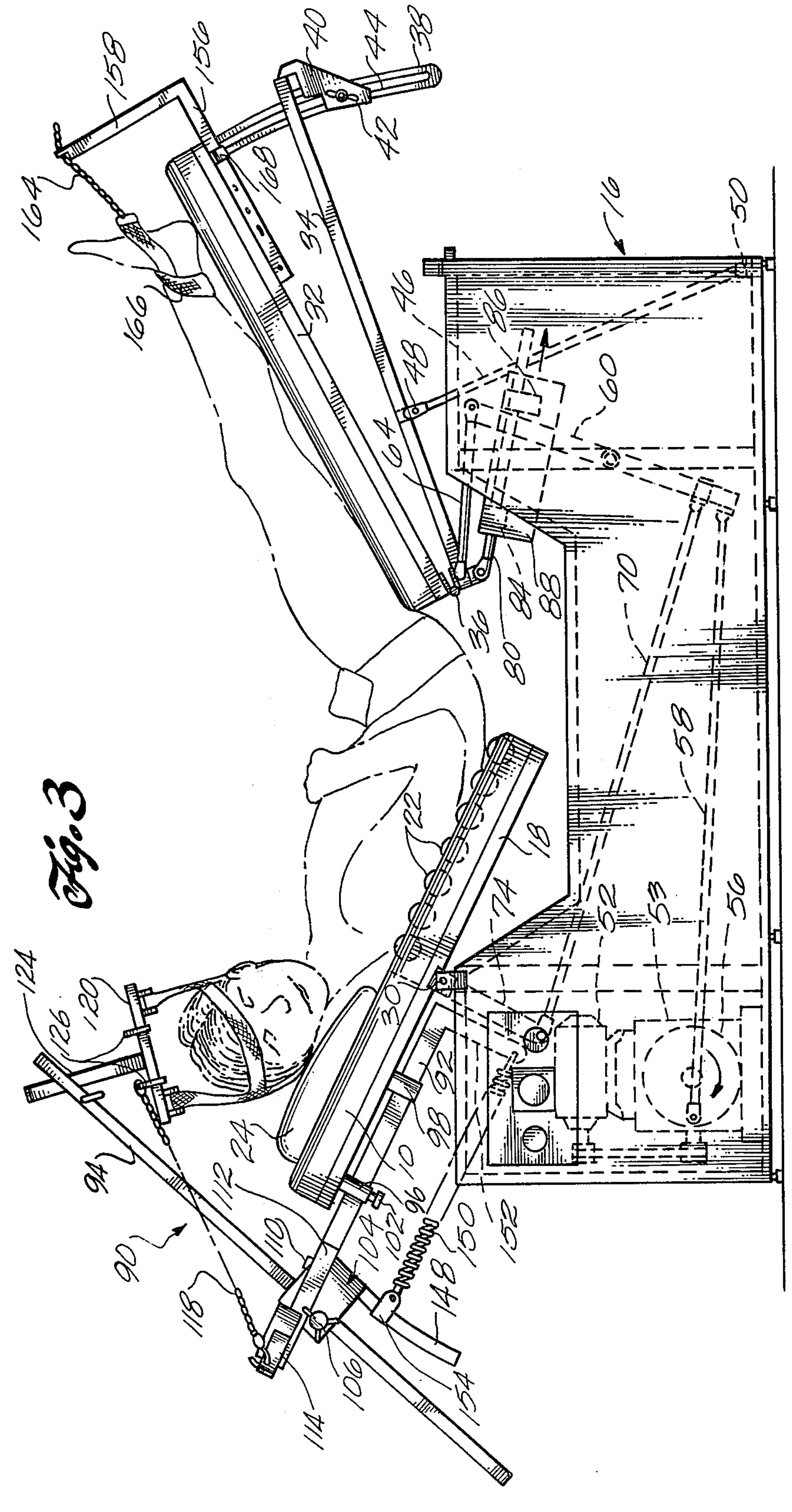
FIG. 3 is an elevation view showing the table of FIG. 2 in a lowered position applying controlled flexion and traction to the lower back and neck of the patient.
Figure 4:
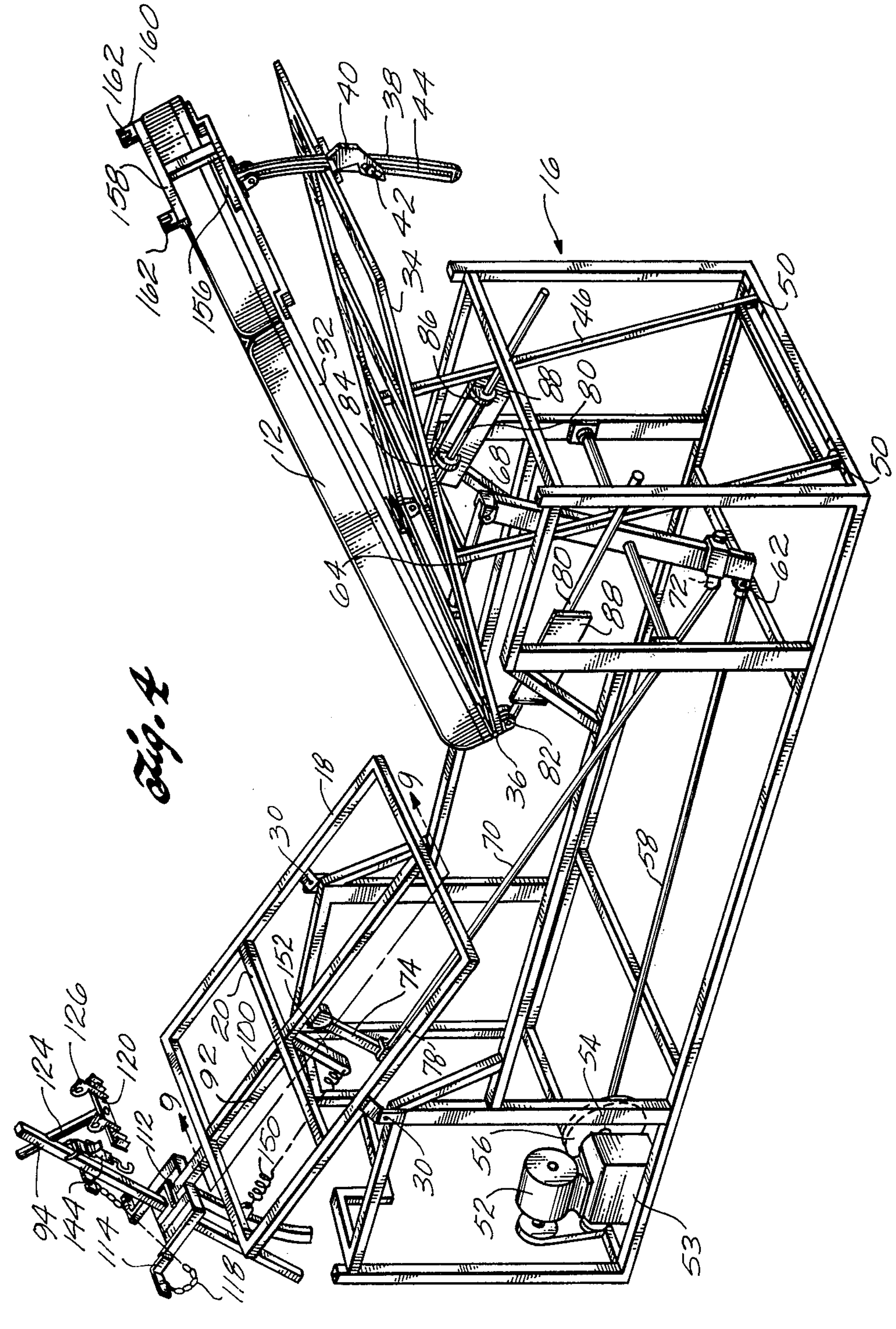
FIG. 4 is a perspective view showing the structural famework and drive means for the table.

The platform support structure and the mechansim for tilting the platform is understood best by referring to FIGS. 2 through 4. An upright rectangular subframe 16 supports the platforms. Referring to FIG. 4, the subframe 16 comprises a rigid skeleton framework of upright posts interconnected with horizontal bracing members all of welded square tubing. The upper and lower platforms 10 and 12 pivot in the open space within the subframe 16. The upper platform 10 includes a rectangular frame 18 having a transverse cross-brace 20 at about the upper one-third of the frame. The frame 18 is of welded square tubing and supports a series of longitudinally spaced apart foam padded rollers 22 extending form about the lower two-thirds of the length of the upper platform 10. The upper one-third of the platform has a longitudinally slidable head support 24. As shown best in FIG. 7, the opposite ends of each padded roller 22 are mounted on corresponding bearings 26 secured to opposite sides of the upper platform frame 18. The head support 24 is slidable relative to the front portion of the upper platform 10 on laterally spaced apart, roller-mounted guide track assemblies 28 on opposite sides of the head support.

The upper platform frame 18 is hinged to the subframe 16 by a separate bearing 30 on each side of the upper platform. The bearings 30 are located at about the mid-point of the length of the frame 18 and allow the upper platform 10 to pivot about a transverse axis through the bearings.

The lower platform 12 comprises a plywood base 32 for carrying the padded upper portion of the platform. The base 32 can rest on a rectangular frame 34 of welded square tubing. A piano-type hinge 36 extends transversely across the inner edge of the lower platform 12 to hinge the padded portion of the platform and the base 32 to the frame 34. The hinge 36 enables the padded support to pivot relative to the frame 34 so that the foot portion of the lower platform 12 can be elevated relative to the platform's inner marginal edge.

A curved elongated arm 38 extends downwardly from the outer edge of the lower platform base 32. The arm 38 is curved about a transverse axis through the hinge 36. The top of the arm 38 is secured to the underside of the base 32, and the lower portion of the curved arm extends downwardly adjacent the side of a bracket 40 which, in turn, extends below the outer edge of the lower platform frame 34. An adjustable clamp 42 extends through the bracket 40 and rides in a curved groove 44 extending lengthwise through the arm 38. The arm 38 is slidable vertically relative to the bracket, and the clamp 42 is used to releasably secure the arm 38 to the bracket 40 to hold the outer end of the lower platform 12 in a fixed elevated position with respect to the lower platform frame 34.

The lower platform frame 34 is supported by the upper ends of an upwardly opening U-shaped frame 46. The upper ends of the U-frame 46 are hinged to a cross-member of the frame 34 located about one-third the longitudinal distance from the inner edge to the outer edge of the frame 34. The ends of frame 46 are attached to the cross-member by bearings 48. The bottom of the frame also is hinged to pivot through bearings 50 mounted on the bottom portion of the subframe 16. The frame 46 pivots about the the bearings 48, 50 to support the lower platform frame 34 as the frame pivots between a horizontal rest position (shown in FIG. 2) and an inclined position (shown in FIG. 3). This governs the degree of elevation of the distal end of the lower frame.

The drive mechanism for the upper and lower platforms 10 and 12 includes a drive motor 52 and gear reduction 53 having a rotary output shaft 54. A disc 56 is secured to the output shaft 54. Rotation of the drive motor reciprocates a longitudinally extending drive shaft 58 attached eccentrically to the disc 56. The drive end of the drive shaft 58 is secured to the bottom of an upwardly extending short connecting rod 60. The short connecting rod 60 is pivotally affixed to the subframe 16 by a transverse fixation rod 61 extending through the anatomical mid-section of the connecting rod 60. The fixation rod 61 rotates in bearings secured to opposite sides of the subframe 16. The rod 60 extends upwardly toward the lower platform 12, and a bearing 62 secures the bottom of the short connecting rod to the drive end of the drive shaft 58. The upper end of the short connecting rod 60 is engaged with a crank arm 64 secured to the mid-point of the inner edge of the lower platform frame 34. A bearing 66 hinges the inner end of the crank arm 64 to the frame 34, and a bearing 68 hinges the outer end of the crank arm 64 to the top of the short connecting rod 60.

A lower portion of the short connecting rod 60 is secured to a longitudinally extending long connecting rod 70 which extends along an upwardly inclined angle from the connecting rod 60 back toward the upper platform 10. A bearing 72 hinges the lower end of the long connecting rod 70 to the short connecting rod 60. The upper end of the long connecting rod 70 is secured to a crank arm 74 which extends downwardly from the midpoint of the upper platform frame 18. The crank arm 74 is a piece of square tubing welded to the underside of a brace member 76 which extends along the longitudinal axis of the frame 18. A bearing 78 hinges the upper end of the long connecting rod 70 of the bottom of the crank arm 74.

When the drive motor rotates the disc 56, the drive shaft 58 reciprocates longitudinally between a fully extended position shown in FIG. 2 and a fully retracted position shown in FIG. 3. In the fully extended position the connecting rods 60 and 70 move their corresponding crank arms 64 and 74 which, in turn, moves the lower and upper frames 34 and 18, respectively, to their horizontal rest positions. When the drive shaft 58 reciprocates to its fully retracted position, the crank arm 64 for the lower platform 12 is forced toward the foot of the lower platform. This causes the crank arm 64 to move the lower platform frame 34 downwardly and away from the upper platform to rotate the lower platform, via the frame 46, about a transverse axis through the bearings 48. When the drive shaft 58 is in its fully retracted position it also moves the upper end of the connecting rod 70 upwardly away from the lower platform. This rotates the crank arm 74 about a transverse axis through the bearings 30 which, in turn, pivots the upper platform 10. Thus, continued reciprocating movement of the drive shaft 58 reciprocates the upper and lower platforms cyclically between their horizontal rest positions, shown in FIG. 2, and their upwardly inclined positions, shown in FIG. 3, in which the separation space between the inner edges of the platforms is increased and the head and foot portions of the platforms are elevated relative to their inner edges.

During reciprocating motion of the platforms, the inner edge of the lower platform 12 is guided to move back and forth along an essentially linear path. The linear guide mechanism includes a pair of laterally spaced apart, longitudinally extending guide rods 80 secured to opposite corners of the lower platform frame 34 at its inner edge. The guide rods 80 are one-inch diameter steel rods. They extend under the lower platform frame 34 toward the foot of the lower platform. The guide rods 80 preferably extend downwardly at an angle of about 15° relative to horizontal. The forward end of each guide rod is secured to the underside of the lower platform frame 34 by corresponding bearings 82. The rear portion of each guide rod slides longitudinally in a pair of longitudinally spaced apart Rulon bearings 84 and 86 mounted on the inside surface of corresponding bearing mounting blocks 88 secured to opposite side panels of the table lower subframe structure. The guide rods 80 control the linear downward movement of the inner marginal edge of the lower platform as the outer end of the platform tilts upwardly during use. As the outer end tilts upwardly, the guide rods are displaced distally in the direction of the arrow shown in FIG. 3. The pivotal motion of the lower platform's inner marginal edge is controlled by the linear direction of movement of the guide rods, and the upward tilt of the platform's outer edge is controlled by the placement of the upright arms of the frame 46.

An upper traction and flexion adjusting mechanism 90 is located adjacent the head of the upper platform 10 and is centered on the longitudinal axis of the table. The mechanism 90 includes an essentially horizontally slidable elongated support rod 92 extending longitudinally under the upper platform 10. The support rod 92 extends generally parallel to the upper platform frame 18 and also extends axially with respect to the frame. The outer end of the support rod 92 extends beyond the outer edge or head of the upper platform frame 18 to support a vertically slidable elongated flexion-adjusting arm 94. The horizontal support rod 92 is slidable longitudinally in a pair of longitudinally spaced apart front and rear brackets 96 and 98, respectively, which extend downwardly from an axial brace 100 in the upper platform frame 18. The front bracket 96 carries an adjusting screw 102 for adjusting the longitudinal position of the support rod 92 with respect to the frame 18. The adjusting screw is used to set the lengthwise position of the support rod 92 with respect to the upper platform frame 18 in accordance with the height of the patient.

The flexion-adjusting arm 94 slides vertically up and down in a rotatable bearing-mounting bracket 104. A rotatable thumbwheel setscrew 106 extends through a portion of the bracket 104 to releasably secure the flexion-adjusting arm 94 in a desired vertical orientation relative to the bracket 104. Bearings 108 rotatably mount the bracket 104 to the front end of the traction support rod 92. In use, the support rod 92 remains stationary, and the bracket 104, together with the flexion-adjusting arm 94 rotates toward and away from the head of the table about a transverse axis through the bearings 108. A transverse stop bar 110 bridges the top of the bracket 104 and remains stationary during rotation of the bracket. The stop bar is engaged by the arm 94 during forward rotation of the bracket (toward the head of the table shown in FIG. 3) to limit maximum rotation of the arm toward the patient.

The front end of the support rod 92 also carries a stationary U-shaped fork 112 which opens away from the head of the table. The fork extends around opposite sides of the rotatable bracket 104, and the foremost ends of the fork extend beyond the flexion-adjusting arm 94 where they support a pair of L-shaped brackets 114. A horizontal chain support bracket 116 is secured to the front face of the flexion-adjusting arm 94 above the fork, and a pair of laterally spaced apart chains 118 extend from the brackets 114 on the fork to the bracket 116 on the adjustment arm 94. The chains 118 hang loosely between the brackets 114 and 116 when not in use, as will be described below.

A rotatable harness support 120 is carried on a top portion of the flexion-adjusting arm 94. The harness support comprises a laterally extending plate which rotates about a pivot pin 122 carried on an adjustable extension 124 projecting toward the table from the vertical adjustment rod 94. The harness support 120 carries a separate upright chain-holding bracket 126 on each side of its axis of rotation. The bracket 126 has separate holes 127 for releasable attachment to one of the chains 118 for a purpose described below. The harness support also carries a separate harness bracket 128 on each side of its axis of rotation.

A head harness or halter 130 is attached to the bracket 128. The head harness includes a narrow strip 132 for extending under the chin of a patient and a wider strap 134 for extending under the occipital region of the patient's head. The harness is secured to the brackets 128 by a pair of adjustable straps 136.

The flexion-adjusting arm 94 is adapted to carry a forearm harness (shown in FIG. 6) which includes an elongated padded arm support 138, spaced apart straps 140 secured to the padded support and adapted for releasable attachment to a patient's forearms, a loop 142 secured to the support between the arm straps 140, and an adjustable strap 144 having one end releasably secured to the loop 140 and its opposite end secured to a U-shaped bracket 146 carried on the flexion-adjusting arm 94. The flexible straps 140 have cooperating sections of Velcro material to provide releasable adjustment for various forearms sizes. The padded forearm support is adapted for releasable attachment to the free end of the strap 144.

The upper traction and flexion adjusting mechanism 90 has a traction-adjusting system which includes a curved support arm 148 extending downwardly from the bracket 104 which rotates with the flexion-adjusting arm 94. An elongated coil spring 150 extends axially with respect to the table between the arm 148 and a downwardly projecting fixed arm 152 at the rear of the horizontal support rod 92. An adjustable clamp 154 releasably secures the front end of the coil spring 150 to the curved arm 148. The clamp is releasable to allow the spring's point of support on the arm 148 to be adjustable in elevation relative to the arm 148. The lower the spring's point of attachment on the arm 148, the greater the tension in the spring, and vice versa. The clamp can be tightened to hold the spring in a position for controlling the desired spring tension.

The lower leg fixing mechanism is secured to the foot of the lower platform 12. The mechanism includes an elongated slidable support arm 156 extending horizontally under the foot of the lower platform, and an upright T-shaped fork 158 extending upwardly from the outer end of the arm. The opposite ends of the fork carrying respective upwardly projecting chain-holding brackets 160 each having a corresponding opening 162 for releasably securing a respective chain 164. The opposite ends of the chains carrying separate leg straps 166 for being releasably secured around the patient's ankles. The support arm 156 is slidably disposed in a bracket 168 located under the lower platform 12. The arm slides axially with respect to the table, and the fork is releasably securable in a fixed position axially to compensate for the height of the patient.

A pair of pelvic straps 170 are located at the marginal inner edge of the lower platform 12. The pelvic straps 170 are secured to the upper padded portion of the lower platform. The free end of each strap has a separate Velcro fastener 172 for use in releasably securing the straps around the pelvic area of a patient lying on the table. The straps are sufficiently long to fit under the patient and be wrapped around the patient's pelvic region and secured at the front pelvic region of the patient.

In using the orthopedic table, a patient lies on the table on his back with the upper portion of this body or trunk supported on the upper platform 10 and the lower portion of his body supported on the lower platform 12. Preferably, the lower edge of the patient's buttocks rests on the inner marginal edge of the lower platform 12. The pelvic straps are crossed over one another under the patient's buttocks and wrapped around the patient's pelvis over the anterior spines where they are secured with the Velcro fasteners. In the rest position of the table (shown in FIG. 2), the patient's buttocks and his lower back rest on the padded rollers 22 and the patient's head rests on the sliding head support 24. The upper traction and flexion adjusting mechanism 90 is used to hold the patient either by his head or by his arms. The head harness is used when cervical traction and flexion are desired. In this instance the head harness is secured to the patient's head, as illustrated in FIGS. 2 and 3. The rear strap 134 is placed under the occipital region of the patient's head to apply traction primarily to the occipital region of the patient's head during tilting of the platforms.

Figure 1:
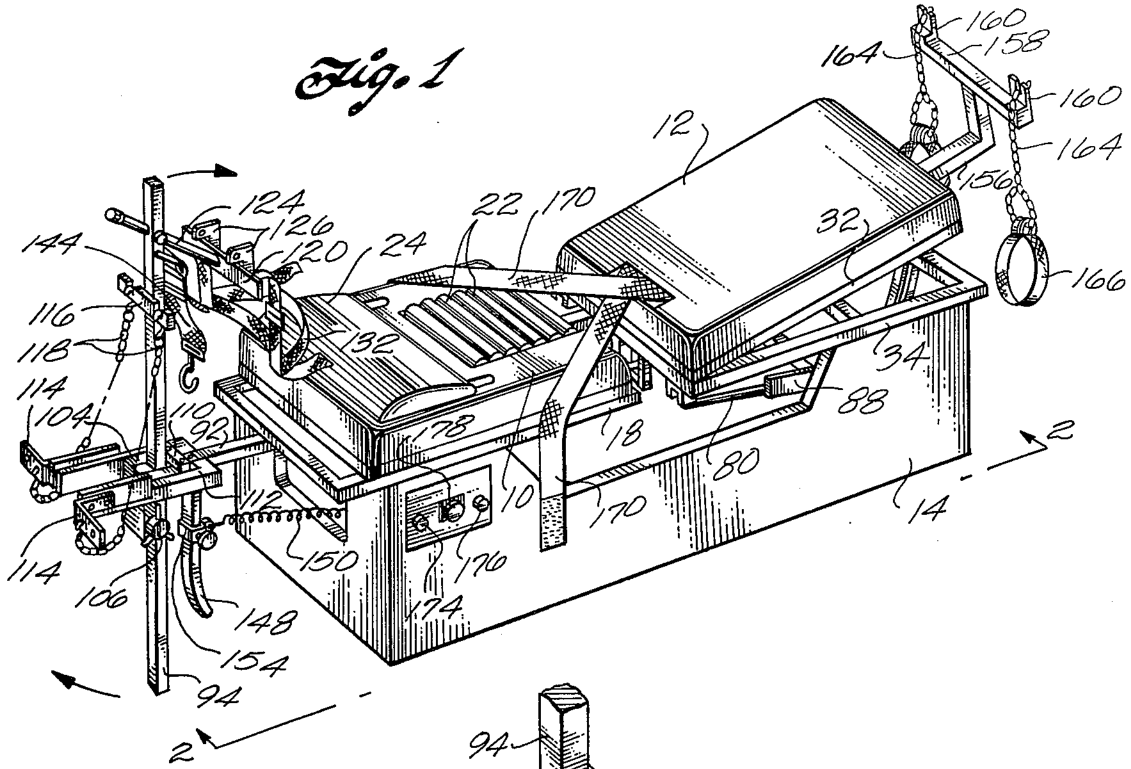
FIG. 1 is a perspective view showing an improved orthopedic table according to this invention.
Figure 5:
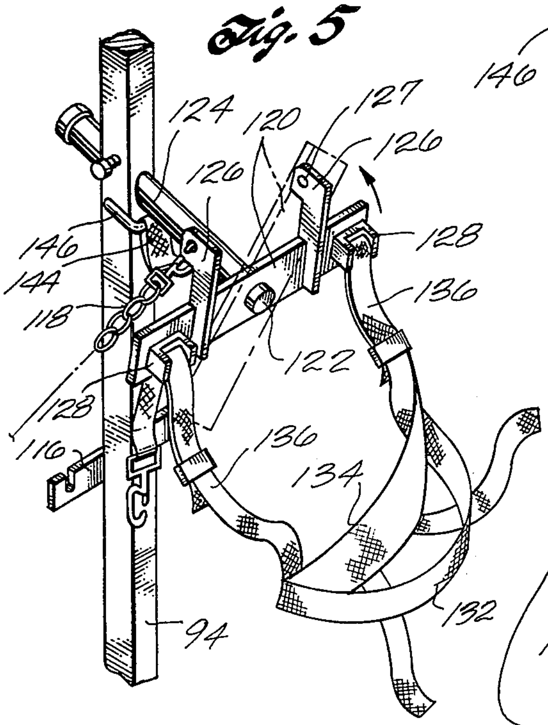
FIG. 5 is a fragmentary perspective view showing a head harness for holding the patient in traction on the table.
Figure 6:
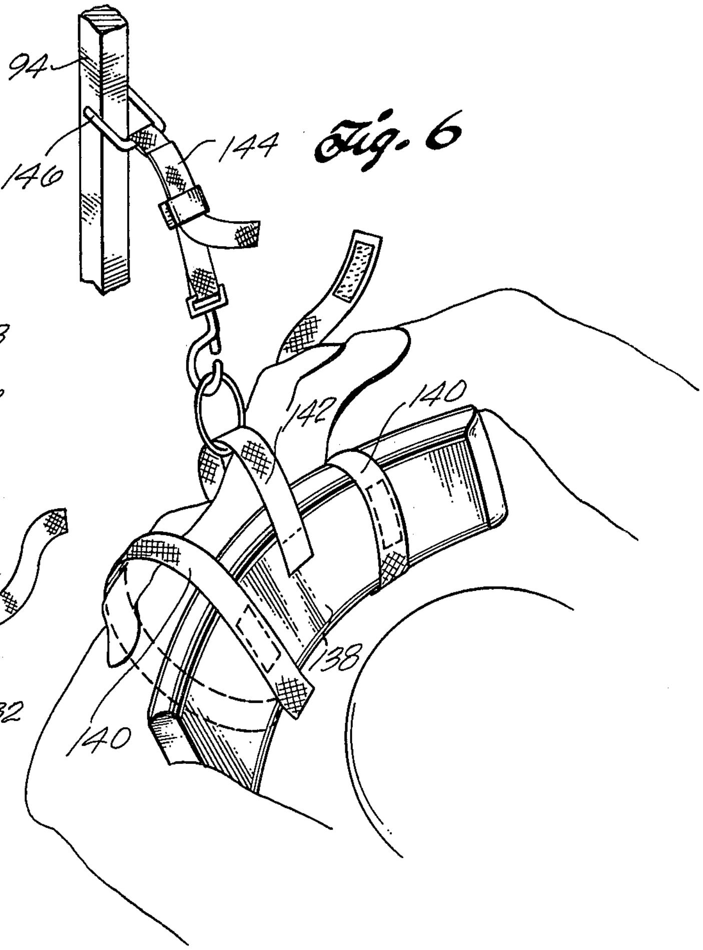
FIG. 6 is a fragmentary perspective view showing a harness for the patient's arms for holding the patient in traction.

Alternately, the patient can be held by the arms to apply greater traction than that applied when the patient's head is harnessed. The arm support also is used when shoulder flexion is applied. In this instance the patient folds his arms above his head as shown in FIG. 6. The forearm support is then attached to the strap 144, and the support is then secured to the patient's forearms as shown in FIG. 6.

To provide traction for the patient's lower body, the leg straps 166 are secured around the patient's ankles to hold the patient's legs and feet in a fixed position on the lower platform 12.

The table is then operated to move the upper and lower platforms between the relatively horizontal rest position shown in FIG. 2 and the tilted position shown in FIG. 3. The platform controls include start and reset buttons 174 and 176, respectively, and a timer switch 178 to set the length of time for the patient's treatment. Preferably, the platform drive mechanism pivots the platforms at a rate of 5 cycles per minute. This timing is considered optimal for improvement in circulation and relaxation of the patient's muscles. Traction is applied to the patient's upper body and to the hamstrings of the patient's legs during cycling of the table. Traction forces blood out of the soft tissues and release of traction permits blood to return.

By simultaneously lowering the inner edge of each platform and raising the outer edge of the platforms, traction is applied to the patient's lower back and hamstrings. The cycling of the table also forces the patient's lower back (lumbar spine) into flexion in the separation space formed between the upper and lower platforms. The pelvic straps 170 perform several functions. They (1) provide support beneath the patient's buttocks in the space between the tilted platforms, (2) kept the patient's thighs secured to the lower platform during cycling of the platforms, and (3) tighten around the patient's pelvis and apply downward force to the front of the patient's pelvis each time the platforms are tilted upwardly. This forces the patient's lower back into flexion, i.e., into a rounded position in the open space between the tilting platforms. The patient's lower back and buttocks lose support as the platforms tilt upwardly so that a portion of the patient's body weight in its flexed position, as well as the applied traction, tends to stretch contractures of the lower back and hamstrings.

Controlled flexion is applied to the patient's lower back by the ability of the lower platform to pivot at its inner edge. The foot region of the lower platform can be elevated to a predetermined angle relative to the subframe. This provides adjustments in the flexion applied to the patient's lower back as the platforms tilt upwardly. That is, as the contractures of the patient's hamstrings permit, the foot end of the lower platform can be manually elevated so as to produce maximum tolerable stretching of the hamstrings. Inasmuch as the hamstrings attach to the lower posterior pelvis, increased elevation of the lower platform tilts the pelvis forward, rounding the patient's lower back and producing more flexion in that region during cycling of the table.

The pelvic straps fix the pelvis to the lower platform with the lower edge of the buttocks resting on the inner edge of the lower platform. This also permits traction to the arms to be more effectively transmitted to the lower back and causes more stretching of the hamstrings.

As described above, the inner marginal edge of the lower platform 12 moves downwardly along an essentially linear path. This applies constant and substantially the same amount of traction to each patient's back and hamstrings largely independently of the patient's body weight. This allows the physician to accurately control the amount of traction applied to each patient.

The angle for cervical or arm traction and the magnitude of the applied traction are adjustable. For cervical traction, the head halter applies traction primarily to the occipital region of the patient's head. Alternatively, where a larger amount of traction is required, the forearm support is used instead of the head halter to apply traction to the patient's upper body. In either instance, the magnitude of the traction is adjustable by the selected position of the coil spring 150 on the curved traction-adjusting arm 148. As the spring's point of support on the arm 148 is lowered, the tension in the spring is increased which, in turn, provides a greater resistance to the rotating of the bracket 104 and the arm 94. This increases the amount of traction applied to the patient's upper body.

Controlled flexion also can be applied either to the patient's cervical region, or to the patient's shoulders during cycling of the table. To apply cervical flexion, the patient is supported on the upper platform solely by the head halter. (FIG. 3 illustrates the head halter used to apply straight flexion to the patient's neck region.) During each cycle of the table, the head halter applies cervical traction to the patient's head which tends to force the patient's neck into flexion (the patient's head is forced to rotate toward his chest which rounds the rear curvature of the patient's neck, thus increasing flexion). The amount of flexion applied to the patient's neck can be increased by raising the head halter's adjustable point of support on the vertically adjustable flexion-adjusting arm 94.

To apply flexion to the shoulders, the patient is supported on the upper platform solely by the forearm support. During each cycle of the table the forearm support applies traction which tends to force the patient's shoulders into flexion (the patient's folded forearms tend to be rotated closer to the plane of his back thus increasing flexion). The amount of flexion applied to the patient's shoulders can be increased by lowering the forearm support's adjustable point of support on the flexion-adjusting arm 94.

The upper platform's sliding head support 24 and the padded rollers 22 permit the patient's body to slide down the upper platform substantially without friction. This permits more of the patient's body weight to act as a means for forcing the lower back into flexion. The rollers also produce a massaging action to the patient's lower back.

In addition to applying straight flexion, the head halter also can be used to apply rotation to the patient's neck during cycling of the table. In this instance, either head halter chain 118 is attached to its corresponding bracket 126. For example, to rotate the patient's head to the right side, the right head halter chain 118 is secured to the bracket 126 on the right side of the rotatable halter support 120. During tilting of the table, the patient's body weight pulls on the chain 118, which rotates the bracket about its axis downwardly to the right. This automatically rotates the heat halter to rotate the patient's head to the right side of the patient. As the table returns to its horizontal position, the bracket rotates back to its neutral position to return the patient's head to its normal position. Thus, continued cycling of the table rotates the patient's head to one side of his body, and the direction of rotation of the patient's neck can be easily adjusted by securing one or the other of the head halter chains 118 to the rotatable support bracket 120.

Thus, the invention makes it possible to effectively apply controlled flexion and traction to a patient's lower back and hamstrings, and the amount of traction and flexion are easily adjustable. Further, the invention enables the physician to treat a patient's neck or shoulder regions by applying controlled amounts of flexion to either of these areas and rotation to the neck.

I claim:

1. An orthopedic table for applying controlled flexion to the lower back of a patient comprising:

(a) a table divided in a mid-region of its length to form an upper platform for supporting the back of a patient and a lower platform for supporting the legs of a patient, the platforms having respective inner edges extending across the divided mid-region;

(b) means for tilting the upper and lower platforms about corresponding longitudinally spaced apart pivot axes to increase the mid-region separation between the inner edges of the platforms;

(c) means for holding a lower portion of the patient's body in a fixed position on the lower platform;

(d) pelvic strap means secured to the lower platform and extendible under a rear pelvic region of the patient's body and extendible over a front pelvic region of the patient's body to hold the patient's pelvic region in a fixed position on the lower platform, and means for securing the pelvic strap means tightly around the pelvic region of the patient to force the patient's lower back into flexion in the separation space between the platforms in response to increased pressure on the front pelvic region of the patient from the pelvic strap means during separation of the platforms;

(e) means for holding an upper portion of the patient's body to apply traction to the patient's body during separation of the platforms; and (f) means for releasably securing the lower platform in a desired angle of inclination to selectively control the amount of flexion applied to the patient's lower back during separation of the platforms;

(g) the means for tilting the lower platform including means for moving the inner edge of the lower platform along a substantially straight path during separation of the platforms to produce substantially constant traction on the patient's lower back and hamstrings.

2. Apparatus according to claim 1 in which the lower platform has an outer edge spaced longitudinally from its inner edge; and including means for positioning the outer edge of the lower platform in an elevated position relative to the inner edge of the platform, and means for releasably holding the lower platform in said relative elevated position during separation of the platforms.

3. Apparatus according to claim 2 in which the lower platform includes a frame, means to pivot the frame about a transverse axis with respect to the longitudinal extent of the table to provide said mid-region separation, a support surface carried by the frame, and means for raising an outer edge of the support surface relative to the frame to produce said elevated position of the lower platform.

4. Apparatus according to claim 1 in which the tilting means includes means for reciprocally tilting the upper and lower platforms about corresponding pivot axes to lower and raise the inner edges of the platforms in unison during reciprocal motion of the platforms.

5. Apparatus according to claim 1 including a series of longitudinally spaced apart rollers on a lower portion of the upper platform to reduce friction on the patient's back during separation of the platforms.

6. Apparatus according to claim 1 in which the upper platform includes a longitudinally slidable headrest for reducing friction between the patient and the upper platform.

7. Apparatus according to claim 1 in which the upper holding means includes means for selectively adjusting the amount of traction applied to the patient's upper body.

8. Apparatus according to claim 7 in which the upper holding means includes body support means for being releasably secured to the patient's upper body, and means for applying a resistance force to said body support means to oppose the patient's body weight supported by the body support means; and in which the means for applying said resistance force includes means for selectively adjusting the amount of said resistance force to adjust the traction applied to the patient's upper body.

9. Apparatus according to claim 8 in which the support means comprises a halter for being secured to the occipital region of the patient's head.

10. Apparatus according to claim 8 in which the support means are adapted for releasable attachment to the patient's forearms in a folded position above the patient's head.

11. Apparatus according to claim 1 including flexion adjusting means comprising a harness for being secured to the head of a patient at a location on the upper platform spaced longitudinally from the mid-region of the table, an elongated tension line extending from said harness away from the mid-region of the table, means for anchoring a free end of the tension line remote from the harness, and means for adjusting the angle of inclination of said tension line to control the amount of flexion applied to the patient's neck during separation of the platforms.

12. Apparatus according to claim 11 in which the flexion adjusting means includes a support member, in which the tension line extends from an anchor point on the support member to the harness on the patient's head, and including means for adjusting the elevation of said anchor point to vary the flexion applied to the patient's neck region.

13. Apparatus according to claim 1 including flexion adjusting means comprising body support means for being secured to the arms of a patient at a location on the upper platform spaced longitudinally from the mid-region of the table, an elongated tension line extending from said body support means away from the mid-region of the table, means for anchoring a free end of the tension line remote from the body support means, and means for adjusting the angle of inclination of said tension line to control the amount of flexion applied to the patient's shoulders during separation of the platforms.

14. Apparatus according to claim 13 in which the flexion adjustment means includes a support member, in which the tension line extends from an anchor point on the support member to the body support means on the patient's arms, and means for adjusting the elevation of said anchor point to vary the flexion applied to the patient's shoulder region.

15. Apparatus according to claim 1 in which the means for holding an upper portion of the patient's body includes a harness for being secured to the head of a patient at a location on the upper platform spaced longitudinally from the mid-region of the table, and means for rotating the harness during tilting of the upper platform to apply rotation to the patient's neck region.

16. Apparatus according to claim 15 including a support rotatable about an axis generally parallel to the longitudinal axis of the table, and a tension line extending from the head harness to an anchor point on the rotatable support spaced from its axis of rotation.

17. Apparatus according to claim 1 in which the pelvic strap means are secured to the upper surface of the lower platform at its inner edge and extends away therefore toward the upper platform, and releasable fastening means on the strap means for adjusting the amount of pelvic pressure applied around the patient's pelvis by the pelvic strap means.

18. An orthopedic table for applying controlled flexion to the body of a patient comprising:

(a) a table divided in a mid-region of its length to form an upper platform for supporting the back of a patient and a lower platform for supporting the legs of a patient, the platforms having respective inner edges extending across the divided mid-region and having respective outer edges spaced longitudinally from the inner edges thereof;

(b) means for tilting the upper and lower platforms about corresponding longitudinally spaced apart pivot axes to increase the mid-region separation between the inner edges of the platforms;

(c) means for holding a lower portion of the patient's body in a fixed position on the lower platform;

(d) means for holding an upper portion of the patient's body to apply traction to the patient's body during mid-region separation of the platforms, a support for supporting said upper holding means, and means for selectively adjusting the angle of inclination of said upper holding means, between said support member and the upper holding means' point of attachment to the patient's upper body, for controlling the amount of flexion applied to the patient's upper body during separation of the platforms;

(e) pelvic strap means secured to the lower platform and extendible under a rear pelvic region of the patient's body and extendible over a front pelvic region of the patient to hold the patient's pelvic region in a fixed position on the lower platform, and means for securing the pelvic strap means tightly around the pelvic region of the patient to force the patient's lower back into flexion in the separation space between the platforms and in response to increased pressure on the front pelvic region of the patient from said pelvic strap means during mid-region separation of the platforms; and (f) means for releasably securing the lower platform in a desired angle of inclination to selectively control the amount of flexion applied to the patient's lower back during separation of the platforms;

(g) the means for tilting the lower platform including means for moving the inner edge of the lower platform along a substantially straight path during mid-region separation of the platforms to produce substantially constant traction on the patient's lower back and hamstrings.

19. Apparatus according to claim 18 in which the upper platform includes a longitudinally slidable head-rest for reducing friction between the patient and the upper platform.

20. Apparatus according to claim 18 in which the upper holding means includes body support means for being releasably secured to the patient's upper body, and including means for applying a resistance force to said body support means to oppose the patient's body weight supported by the body support means, and means for selectively adjusting the amount of said resistance force to adjust the traction applied to the patient's upper body.

21. Apparatus according to claim 20 in which the body support means comprises a halter for being secured to the occipital region of the patient's head.

22. Apparatus according to claim 20 in which the body support means are adapted for releasable attachment to the patient's forearms in a folded position above the patient's head.

23. Apparatus according to claim 18 in which the upper holding means includes a harness for being secured to the head of a patient at a location on the upper platform spaced longitudinally from the mid-region of the table, and including flexion adjusting means including an elongated tension line extending from said harness away from the mid-region of the table, means for anchoring a free end of the tension line remote from the harness, and means for adjusting the angle of inclination of the anchor tension line to control the amount of flexion applied to the patient's neck during separation of the platforms.

24. Apparatus according to claim 23 in which the tension line extends from an anchor point on the support member to the harness on the patient's head, and means for adjusting the elevation of said anchor point to vary the flexion applied to the patient's neck region.

25. Apparatus according to claim 18 in which the upper holding means includes body support means for being secured to the arms of a patient at a location on the upper platform spaced longitudinally from the mid-region of the table, and including flexion adjusting means including an elongated tension line extending from said body support means away from the mid-region of the table, means for anchoring a free end of the tension line remote from the body support means, and means for adjusting the angle of inclination of said tension line to control the amount of flexion applied to the patient's shoulders during separation of the platforms.

26. Apparatus according to claim 25 in which the tension line extends from an anchor point on the support member to the means of support on the patient's arms, and means for adjusting the elevation of said anchor point to vary the flexion applied to the patient's shoulder region.

27. Apparatus according to claim 18 in which the upper holding means includes a harness for being secured to the head of a patient at a location on the upper platform spaced longitudinally from the mid-region of the table, and means for rotating the harness during tilting of the upper platform to apply rotation to the patient's neck region.

28. Apparatus according to claim 18 in which the pelvic strap means are secured to the upper surface of the lower platform at its inner edge and extend away therefrom toward the upper platform, and releasable fastening means for adjusting the amount of pelvic pressure applied around the patient's pelvis by the pelvic strap means.

* * * * *

UNITED STATES PATENT AND TRADEMARK OFFICE

CERTIFICATE OF CORRECTION

PATENT NO. : 4,144,880

DATED : March 20, 1979

INVENTOR(S) : E. ROBERT DANIELS

It is certified that error appears in the above-identified patent and that said Letters Patent are hereby corrected as shown below:

Column 2, line 56, "famework" should read -- framework --. Column 3, line 50, "form" should read -- for -- . Column 7, line 29, "carrying" should read -- carry -- ; line 50, "this" should read -- his -- . Column 8, line 37, "kept" should read -- keep -- . Column 9, line 65, "heat" should read -- head -- . Column 12, line 20, "therefore" should read -- therefrom -- .

Signed and Sealed this

*Twenty-fourth* Day of *July 1979*

[SEAL]

*Attest:*

LUTRELLE F. PARKER

*Attesting Officer* *Acting Commissioner of Patents and Trademarks*